(12) United States Patent
Austen

(10) Patent No.: US 10,327,800 B2
(45) Date of Patent: Jun. 25, 2019

(54) METHOD AND APPARATUS FOR SKIN RESURFACING

(71) Applicant: The General Hospital Corporation, Boston, MA (US)

(72) Inventor: William G. Austen, Weston, MA (US)

(73) Assignee: The General Hospital Corporation, Boston, MA (US)

( * ) Notice: Subject to any disclaimer, the term of this patent is extended or adjusted under 35 U.S.C. 154(b) by 258 days.

(21) Appl. No.: 15/250,882

(22) Filed: Aug. 29, 2016

(65) Prior Publication Data
US 2016/0367280 A1    Dec. 22, 2016

Related U.S. Application Data

(63) Continuation of application No. 13/982,121, filed as application No. PCT/US2012/022993 on Jan. 27, 2012, now Pat. No. 9,439,673.
(Continued)

(51) Int. Cl.
*A61B 17/3205* (2006.01)
*A61B 17/20* (2006.01)
(Continued)

(52) U.S. Cl.
CPC .... *A61B 17/32053* (2013.01); *A61B 10/0233* (2013.01); *A61B 17/205* (2013.01);
(Continued)

(58) Field of Classification Search
CPC ............ A61B 17/205; A61B 17/32053; A61B 2017/00747; A61B 17/3205;
(Continued)

(56) References Cited

U.S. PATENT DOCUMENTS 3,001,522 A    9/1961    Silverman
3,683,892 A    8/1972    Harris
(Continued)

FOREIGN PATENT DOCUMENTS

CA    2361777 A1    5/2002
CN    201005966 Y    1/2008
(Continued)

OTHER PUBLICATIONS

Bedi, et al., The Effects of Pulse Energy Variations on the Dimensions of Microscopic Thermal Treatment Zones in Nonablative Fractional Resurfacing, Lasers in Surgery and Medicine, 2007, 39:145-155.
(Continued)

*Primary Examiner* — Katherine M Shi
(74) *Attorney, Agent, or Firm* — Quarles & Brady LLP

(57) ABSTRACT

Exemplary embodiments of method and apparatus are provided for resurfacing of skin that includes formation of a plurality of small holes, e.g., having widths less than about 1 mm or 0.5 mm, using a mechanical apparatus, thus avoiding generation of thermal damage as occurs with conventional laser resurfacing procedures and devices. The holes formed can be well-tolerated by the skin, and can exhibit shorter healing times and less swelling than conventional resurfacing procedures. The apparatus includes one or more needles adapted to remove a small portion of tissue when inserted into and withdrawn from the skin. The fractional surface coverage of the holes can be between about 0.1 and 0.7, or between about 0.2 and 0.5. The exemplary method and apparatus can produce cosmetic effects such as increases in collagen content, epidermal thickness, and dermal/epidermal junction undulations in the skin.

19 Claims, 7 Drawing Sheets

Related U.S. Application Data

(60) Provisional application No. 61/437,486, filed on Jan. 28, 2011.

(51) Int. Cl.
*A61B 10/02* (2006.01)
*A61B 17/00* (2006.01)

(52) U.S. Cl.
CPC ............... *A61B 2017/00761* (2013.01); *A61B 2017/00765* (2013.01)

(58) Field of Classification Search
CPC ...... A61B 2017/00761; A61B 10/0233; A61B 10/0275; A61B 17/322; A61B 2010/0208; A61B 2010/0225; A61B 2017/00561; A61B 2017/00752; A61B 2017/00769; A61B 2017/0096
USPC ............ 600/562, 566, 567; 606/131, 186, 9; 604/506
See application file for complete search history.

(56) References Cited

U.S. PATENT DOCUMENTS

| | | |
|---|---|---|
| 3,929,123 A | 12/1975 | Jamshidi |
| 4,108,096 A | 8/1978 | Ciecior |
| 4,649,918 A | 3/1987 | Pegg et al. |
| 4,865,026 A | 9/1989 | Barrett |
| 4,903,709 A | 2/1990 | Skinner |
| 5,269,316 A | 12/1993 | Spitalny |
| 5,458,112 A | 10/1995 | Weaver |
| 5,615,690 A | 4/1997 | Giurtino et al. |
| 5,749,895 A | 5/1998 | Sawyer et al. |
| 5,885,211 A | 3/1999 | Eppstein et al. |
| 5,922,000 A | 7/1999 | Chodorow |
| 6,022,324 A | 2/2000 | Skinner |
| 6,211,598 B1 | 4/2001 | Dhuler et al. |
| 6,241,687 B1 | 6/2001 | Voegele et al. |
| 6,251,097 B1 | 6/2001 | Kline et al. |
| 6,264,618 B1 | 7/2001 | Landi et al. |
| 6,432,098 B1 | 8/2002 | Kline et al. |
| 6,461,369 B1 | 10/2002 | Kim |
| 6,562,037 B2 | 5/2003 | Paton et al. |
| 6,669,618 B2 | 12/2003 | Reising et al. |
| 6,669,694 B2 | 12/2003 | Shadduck |
| 6,733,496 B2 | 5/2004 | Sharkey et al. |
| 6,893,388 B2 | 5/2005 | Reising et al. |
| 6,936,039 B2 | 8/2005 | Kline et al. |
| 7,073,510 B2 | 7/2006 | Redmond et al. |
| 7,131,951 B2 | 11/2006 | Angel |
| 8,128,639 B2 | 3/2012 | Tippett |
| 8,209,006 B2 | 6/2012 | Smith et al. |
| 8,246,611 B2 | 8/2012 | Paithankar et al. |
| 8,435,791 B2 | 5/2013 | Galun et al. |
| 8,480,592 B2 | 7/2013 | Chudzik et al. |
| 9,439,673 B2 | 9/2016 | Austen |
| 2002/0169431 A1 | 11/2002 | Kline et al. |
| 2003/0088220 A1 | 5/2003 | Molander et al. |
| 2003/0119641 A1 | 6/2003 | Reising |
| 2003/0158521 A1 | 8/2003 | Ameri |
| 2003/0233082 A1 | 12/2003 | Kline et al. |
| 2004/0023771 A1 | 2/2004 | Reising et al. |
| 2004/0073195 A1 | 4/2004 | Cucin |
| 2005/0090765 A1 | 4/2005 | Fisher |
| 2005/0130821 A1 | 6/2005 | Reising et al. |
| 2005/0165329 A1 | 7/2005 | Taylor et al. |
| 2005/0209567 A1 | 9/2005 | Sibbitt, Jr. |
| 2005/0215921 A1 | 9/2005 | Hibner et al. |
| 2005/0215970 A1 | 9/2005 | Kline et al. |
| 2005/0215971 A1 | 9/2005 | Roe et al. |
| 2005/0234419 A1 | 10/2005 | Kline et al. |
| 2005/0245952 A1 | 11/2005 | Feller |
| 2005/0283141 A1 | 12/2005 | Giovannoli |
| 2006/0064031 A1 | 3/2006 | Miller |
| 2006/0116605 A1 | 6/2006 | Nakao |
| 2006/0161179 A1 | 7/2006 | Kachenmeister |
| 2006/0184153 A1 | 8/2006 | Mark et al. |
| 2006/0259006 A1 | 11/2006 | McKay et al. |
| 2007/0038181 A1 | 2/2007 | Melamud et al. |
| 2007/0060888 A1 | 3/2007 | Goff et al. |
| 2007/0073217 A1 | 3/2007 | James |
| 2007/0073327 A1 | 3/2007 | Giovannoli |
| 2007/0078466 A1 | 4/2007 | Bodduluri et al. |
| 2007/0078473 A1 | 4/2007 | Bodduluri et al. |
| 2007/0106306 A1 | 5/2007 | Bodduluri et al. |
| 2007/0156161 A1 | 7/2007 | Weadock et al. |
| 2007/0179455 A1 | 8/2007 | Geliebter et al. |
| 2007/0183938 A1 | 8/2007 | Booker |
| 2007/0198000 A1 | 8/2007 | Miyamoto et al. |
| 2007/0213634 A1 | 9/2007 | Teague |
| 2007/0239260 A1 | 10/2007 | Palanker et al. |
| 2007/0249960 A1 | 10/2007 | Williamson, IV |
| 2007/0270710 A1 | 11/2007 | Frass et al. |
| 2008/0009802 A1 | 1/2008 | Lambino et al. |
| 2008/0009901 A1 | 1/2008 | Redmond et al. |
| 2008/0045858 A1 | 2/2008 | Tessitore et al. |
| 2008/0132979 A1 | 6/2008 | Gerber |
| 2008/0234602 A1* | 9/2008 | Oostman ............ A61B 10/0266 600/564 |
| 2008/0234699 A1 | 9/2008 | Oostman Jr. et al. |
| 2008/0300507 A1 | 12/2008 | Figueredo et al. |
| 2008/0312648 A1 | 12/2008 | Peterson |
| 2009/0227895 A1 | 9/2009 | Goldenberg |
| 2009/0312749 A1 | 12/2009 | Pini et al. |
| 2010/0023003 A1 | 1/2010 | Mulholland |
| 2010/0082042 A1 | 4/2010 | Drews |
| 2010/0121307 A1* | 5/2010 | Lockard ............ A61M 37/0015 604/506 |
| 2010/0160822 A1 | 6/2010 | Parihar et al. |
| 2010/0185116 A1 | 7/2010 | Al-Mohizea |
| 2010/0330589 A1 | 12/2010 | Bahrami et al. |
| 2011/0105949 A1 | 5/2011 | Wiksell |
| 2011/0245834 A1 | 10/2011 | Miklosovic |
| 2011/0251602 A1 | 10/2011 | Anderson et al. |
| 2011/0282238 A1* | 11/2011 | Houser ............... A61B 10/0275 600/564 |
| 2011/0313429 A1* | 12/2011 | Anderson ........... A61B 10/0233 606/131 |
| 2012/0041430 A1 | 2/2012 | Anderson et al. |
| 2012/0136387 A1 | 5/2012 | Redmond et al. |
| 2012/0226214 A1 | 9/2012 | Gurtner et al. |
| 2012/0226306 A1 | 9/2012 | Jackson et al. |
| 2012/0253333 A1 | 10/2012 | Garden et al. |
| 2012/0271320 A1 | 10/2012 | Hall et al. |
| 2013/0045171 A1 | 2/2013 | Utecht et al. |
| 2014/0200484 A1 | 7/2014 | Austen et al. |
| 2014/0277055 A1 | 9/2014 | Austen, Jr. |
| 2014/0296741 A1 | 10/2014 | Austen |
| 2016/0095592 A1 | 4/2016 | Levinson et al. |

FOREIGN PATENT DOCUMENTS

| | | |
|---|---|---|
| CN | 101208128 A | 6/2008 |
| CN | 101232858 A | 7/2008 |
| CN | 101347346 A | 1/2009 |
| DE | 202004010659 U1 | 10/2004 |
| EA | 9092 B1 | 10/2007 |
| EP | 0027974 A1 | 5/1981 |
| EP | 1224949 A1 | 7/2002 |
| EP | 1396230 A1 | 3/2004 |
| EP | 1278061 B1 | 2/2011 |
| EP | 2409727 A1 | 1/2012 |
| JP | 2005000642 A | 1/2005 |
| JP | 2005103276 A | 4/2005 |
| JP | 2009219858 A | 10/2009 |
| JP | 2010515469 A | 5/2010 |
| JP | 2010532178 A | 10/2010 |
| KR | 20100135864 A | 12/2010 |
| RU | 2119304 C1 | 9/1998 |
| RU | 11679 U1 | 11/1999 |
| RU | 50799 U1 | 1/2006 |
| RU | 58359 U1 | 11/2006 |

(56) References Cited

FOREIGN PATENT DOCUMENTS

| | | |
|---|---|---|
| RU | 2308873 C2 | 10/2007 |
| SU | 1426740 A1 | 9/1988 |
| SU | 1801391 A1 | 8/1990 |
| WO | 9322971 A1 | 11/1993 |
| WO | 9929243 A1 | 6/1999 |
| WO | 0141651 A2 | 6/2001 |
| WO | 2006118804 A1 | 11/2006 |
| WO | 2007011788 A2 | 1/2007 |
| WO | 2007024038 A1 | 3/2007 |
| WO | 2007106170 A2 | 9/2007 |
| WO | 2009072711 A2 | 6/2009 |
| WO | 2009099988 A2 | 8/2009 |
| WO | 2009137288 A2 | 11/2009 |
| WO | 2009146053 A1 | 12/2009 |
| WO | 2009146068 A1 | 12/2009 |
| WO | 2010027188 A2 | 3/2010 |
| WO | 2010080014 A2 | 7/2010 |
| WO | 2010097790 A1 | 9/2010 |
| WO | 2012052986 A2 | 4/2012 |
| WO | 2012103483 A2 | 8/2012 |
| WO | 2012103488 A1 | 8/2012 |
| WO | 2012103492 A1 | 8/2012 |
| WO | 2012119131 A1 | 9/2012 |
| WO | 2012135828 A1 | 10/2012 |
| WO | 2013013196 A1 | 1/2013 |
| WO | 2013013199 A2 | 1/2013 |
| WO | 2014179729 A1 | 11/2014 |
| WO | 2015021434 A2 | 2/2015 |

OTHER PUBLICATIONS

CEVC, Review—Biologicals & Immunologicals—Drug Delivery Across the Skin, Expert Opinion on Investigational Drugs, 1997, 6(12):1887-1888.
Chang, An Updated Review of Tyrosinase Inhibitors, International Journal of Molecular Sciences, 2009, 10:2440-2475.
Czech, et al., Pressure-Sensitive Adhesives for Medical Applications, INTECH Open Access Publisher, 2011, pp. 309-332.
Dai, et al., Magnetically-Responsive Self Assembled Composites, Chemical Society Reviews, 2010, 39:4057-4066.
De Las Heras Alarcon, et al., Stimuli Responsive Polymers for Biomedical Applications, Chemical Society Reviews, 2005, 34:276-285.
Dini, et al., Grasping Leather Plies by Bernoulli Grippers, CIRP Annals—Manufacturing Technology, 2009, 58:21-24.
Dujardin, et al., In Vivo Assessment of Skin Electroporation Using Square Wave Pulses, Journal of Controlled Release, 2002, 79:219-227.
Fernandes, et al., Micro-Mechanical Fractional Skin Rejuvenation, Plastic and Reconstructive Surgery, 2012, 130 (5S-1): 28.
Fernandes, et al., Micro-Mechanical Fractional Skin Rejuvenation, Plastic and Reconstructive Surgery, 2013, 131:216-223.
Galaev, 'Smart' Polymers in Biotechnology and Medicine, Russian Chemical Reviews, 1995, 64(5):471-489.
Glogau, Aesthetic and Anatomic Analysis of the Aging Skin, Seminars in Cutaneous Medicine and Surgery, 1996, 15(3):134-138.
Hale, et al., Optical Constants of Water in the 200-nm to 200-μm Wavelength Region, Applied Optics, 1973, 12(3):555-563.
Huang, et al., Shape Memory Materials, Materials Today, 2010, 13(7):54-61.
Kakasheva-Mazenkovska, et al., Variations of the Histomorphological Characteristics of Human Skin of Different Body Regions in Subjects of Different Age, Contributions/Macedonian Academy of Sciences and Arts, Section of Biological and Medical Sciences, 2010 32(2):119-128.
Konermann, et al., Ultrasonographically Guided Needle Biopsy of Benign and Malignant Soft Tissue and Bone Tumors, Journal of Ultrasound in Medicine, 2000, 19(7):465-471.
Lien, et al., A Novel Gripper for Limp Materials Based on Lateral Coanda Ejectors, CIRP Annals—Manufacturing Technology, 2008, 57:33-36.
Majid, Microneedling Therapy in Atrophic Facial Scars: An Objective Assessment, Journal of Cutaneous and Aesthetic Surgery, 2009, 2(1):26-30.
Pliquett, et al., A Propagating Heat Wave Model of Skin Electroporation, Journal of Theoretical Biology, 2008, 251:195-201.
Prausnitz, et al., Electroporation of Mammalian Skin: A Mechanism to Enhance Transdermal Drug Delivery, Proc. Natl. Acad. Sci., 1993, 90:10504-10508.
PCT International Search Report and Written Opinion, PCT/US2014/036638, dated Oct. 2, 2014.
PCT International Preliminary Report on Patentability, PCT/US2014/036638, dated Nov. 3, 2015.
PCT International Search Report and Written Opinion, PCT/US2014/050426, dated Feb. 4, 2015.
PCT International Preliminary Report on Patentability, PCT/US2014/050426, dated Feb. 9, 2016.
PCT International Search Report and Written Opinion, PCT/US2012/022993, dated May 17, 2012.
Bolshaya meditsinskaya entsiklopediya, M., 1976, vol. 3, p. 184.
Bolshaya meditsinskaya entsiklopediya, M., 1986, vol. 27, pp. 480-481.
European Patent Office, Supplementary European Search Report, Application No. 12738813, dated Jun. 12, 2014.
European Patent Office, Extended European Search Report, Application No. 12814711.3, dated Feb. 11, 2015.
PCT International Search Report and Written Opinion, PCT/US2012/022980, dated Aug. 9, 2012.
PCT International Search Report and Written Opinion, PCT/US2012/047708, dated Oct. 18, 2012.
PCT International Search Report and Written Opinion, PCT/US2012/047716, dated Oct. 25, 2012.
Spravochik operatsionnoy I perevyazochnoy sestrie, M., <<Meditsina>>, 1985, p. 31.

* cited by examiner

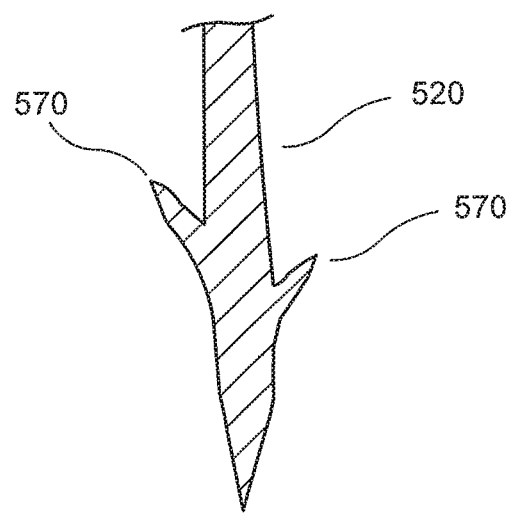
F I G. 5E
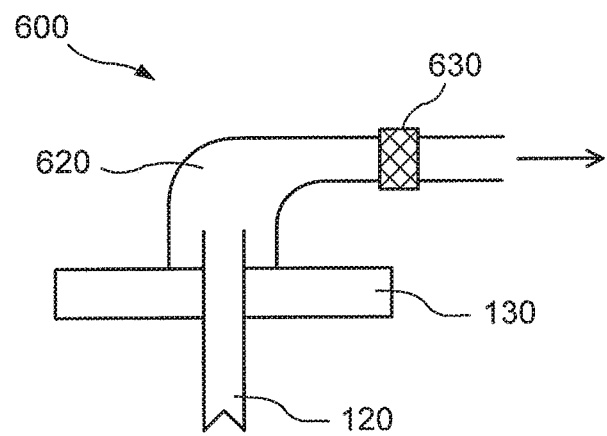
F I G. 6

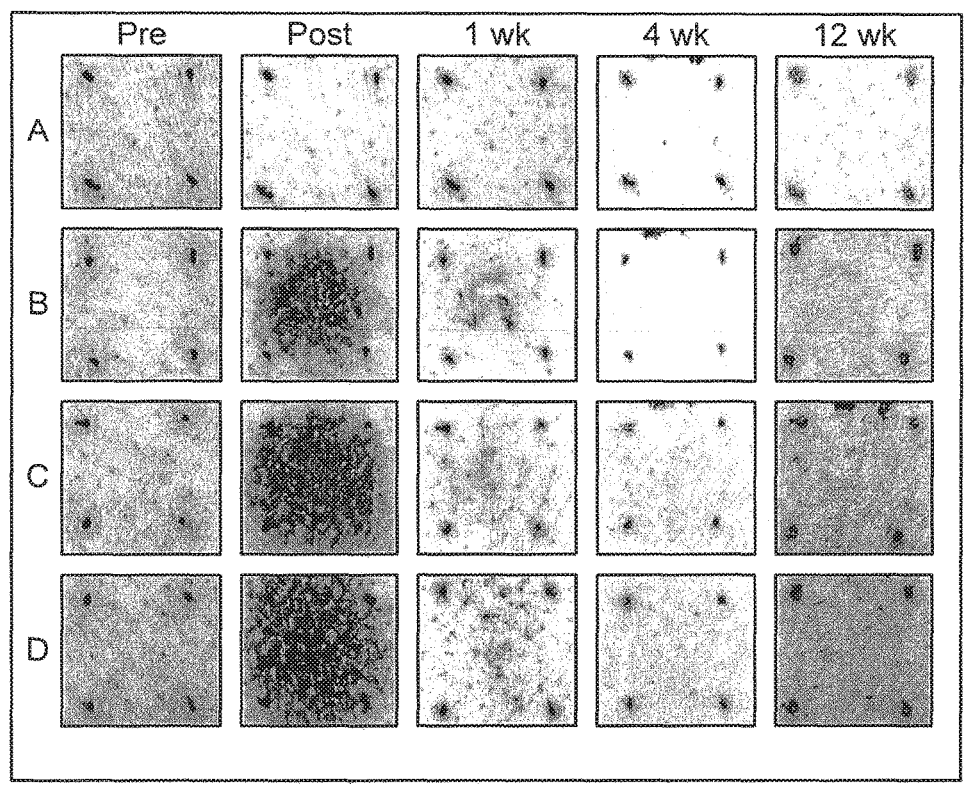
F I G. 7
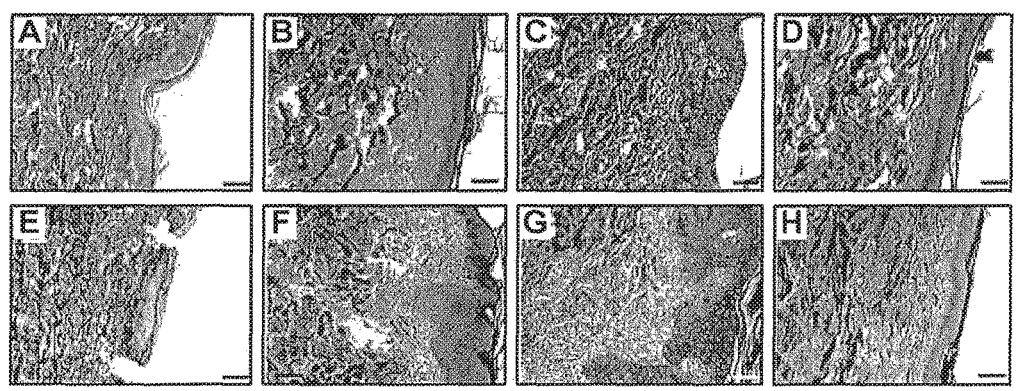
F I G. 8

METHOD AND APPARATUS FOR SKIN RESURFACING

CROSS REFERENCE TO RELATED APPLICATION

This application is a continuation of U.S. patent application Ser. No. 13/982,121 filed Oct. 15, 2013, which represents the US National Stage of International Application PCT/US2012/022993 filed Jan. 27, 2012, which claims priority to U.S. Provisional Patent Application 61/437,486 filed Jan. 28, 2011 all of which are incorporated by reference herein in their entirety for all purposes.

FIELD OF THE PRESENT INVENTION

The present invention relates to cosmetic methods and apparatus for mechanically generating a plurality of small damaged regions in biological tissue, e.g., in skin or the like, which may provide beneficial cosmetic effects such as skin resurfacing and rejuvenation.

BACKGROUND INFORMATION

Skin loses its tone and smooth texture as it ages, commonly developing wrinkles and laxity. This can be further compounded by photodamage and other effects such as, e.g., scarring from acne or trauma, age-related rhytides, and striae. Aged skin is characterized by a flattened dermal-epidermal junction, thinning epidermis and dermis, less fibrous collagen, and alterations in elastin organization. Skin rejuvenation therapies can work to remove these damaged tissues and/or and stimulate the growth of new, healthy collagen, elastic fibers and skin cells and thereby improve the appearance of the skin.

A common procedure for skin rejuvenation, laser resurfacing, uses light energy to heat and damage the upper dermis. However, laser resurfacing has a poor side effect profile, with many patients experiencing prolonged erythema, scarring and dyspigmentation. Recently, the development and use of fractional ablative therapy has achieved better results. A fractional damage can include forming small regions of damage in tissue (e.g., ablation or thermal damage) that are surrounded by healthy tissue. A small size of the damaged regions (e.g., generally less than about 1 mm) and proximity of healthy tissue can facilitate a rapid healing of the damaged regions, as well as other desirable effects such as tissue shrinkage.

Laser-based fractional resurfacing techniques and devices involve the use of expensive and potentially dangerous lasers or other sources of intense optical energy to damaged tissue. Such optical systems can be expensive, present safety hazards, and require a skilled physician or clinician for their operation.

Percutaneous collagen induction therapy (PCI), another approach for mechanically inducing cosmetic improvements in skin tissue, is based on the use of stamps or rollers to insert small solid needles through the epidermis and into the dermis of the skin to stimulate collagen growth. This technique can improve the appearance, e.g., of acne, burn scars and striae without removal of tissue, and may provide an improved side effect profile, but generally has exhibited limited clinical efficacy. Because PCI does not heat the skin, needling devices also avoid the erythema and scaring that may be associated with laser treatment, and have significantly less recovery time.

Accordingly, there may be a need for a relatively simple, inexpensive, and safe cosmetic method and device that can be mechanical in nature and would overcome at least some of such exemplary deficiencies, and can be configured to produce fractional damage in biological tissue that is well-tolerated.

SUMMARY OF EXEMPLARY EMBODIMENTS

The present invention relates to exemplary embodiments of simple, inexpensive, and safe methods and devices for mechanical generation of a plurality of small regions of damage in biological tissue, such as skin. Such exemplary damaged regions can have a size that is, e.g., about 1 mm or less as measured in at least one direction along the tissue surface.

An exemplary embodiment of an apparatus according to the present invention can be provided that includes one or more needles configured to be inserted into and withdrawn from the tissue to remove portions of tissue and thereby generate damaged regions. The exemplary needles can be hollow (e.g., coring needles) or solid, and adapted and/or sized to remove small portions of tissue when inserted into and withdrawn from the tissue. One or more extensions can be provided along an outer surface of the needles and/or an inner surface of the hollow needles to affect the amount, shape, and/or characteristics of tissue removed. One or more notches or slots can be provided that extend at least partially through a wall of the hollow needles. The distal end of the needles can be tapered or pointed to facilitate insertion of the needles into the tissue. Needle tips having two or more points or prongs can be used.

According to further exemplary embodiments of the present invention, a plurality of needles can be affixed or coupled to a substrate, which can facilitate a generation of a plurality of damaged regions using a stamping mode in which the needles are inserted into the tissue substantially simultaneously. In other exemplary embodiments, the needles can be provided on a roller arrangement, e.g., a cylindrical base configured to rotate about its longitudinal axis. Such exemplary apparatus can form a plurality of damaged regions in the tissue when the roller arrangement is rolled over the tissue surface.

The damaged regions can be holes that result from removed portions of tissue, and/or physically disrupted volumes of tissue generated by insertion and subsequent removal of the needle(s). For example, such damaged regions can be generated in regular patterns or arrays, in one or more rows, in random spatial distributions, or in other patterns.

The diameter or width of the holes or damaged tissue regions can be less than about 1 mm, e.g., about 0.8 mm or less, or even about 0.5 mm or less, for example, between about 0.3 mm and 0.5 mm (i.e., between about 300 and 500 microns). Hollow coring needles adapted to form such holes can be formed from conventional syringe needles or the like, having a size between 18 and 30 gauge, which corresponds to internal diameters between about 0.84 mm and 0.14 mm. For example, needle sizes between about 22 and 25 gauge (e.g., internal diameters between about 0.40 mm and 0.24 mm) can be used. Coring needles smaller than 30 gauge or larger than 18 gauge may also be used in certain embodiments.

The fraction of tissue surface area covered by the damaged regions (e.g., the approximate areal fraction of skin tissue removed using one or more coring needles in a treatment area) can be between about 20% and about 70%, or between about 20% and about 50%, or between about 20% and about 40%. Values of this areal coverage (e.g. fraction of surface tissue removal) of between about 20-50%, for example, may be particularly well-tolerated in skin and sufficiently large to promote desirable cosmetic rejuvenation effects (such as increased collagen production and/or thickening of the dermis) while not being so large as to require extended healing times or present post-treatment complications. Larger or smaller exemplary areal coverages can also be generated in further exemplary embodiments of the present invention, e.g., to treat particular regions of skin or other tissues more or less aggressively. A predetermined coverage can be achieved, e.g., by inserting and withdrawing one or more coring needles from a target area of known area for a particular number of times.

In further exemplary embodiments of the present invention, one or more needles can be affixed to a substrate that is mechanically coupled to a reciprocating arrangement. The exemplary reciprocating arrangement can include a motor or other actuator configured to repeatedly insert and withdraw the one or more needles. The reciprocating arrangement can be provided in a housing that facilitates manipulation of the apparatus, e.g., a placement of the apparatus on the tissue being treated and/or traversing the apparatus over the tissue. The housing can optionally be configured to stretch or otherwise stabilize the tissue proximal to the needle(s) being inserted, to reduce deformation of the tissue and/or improve accuracy of the placement of the needle(s) in the tissue. The reciprocating arrangement can further include a translational controller configured to translate the needle(s) over the tissue in at least one direction, and optionally in two orthogonal directions, to provide larger regions of treatment without translating the entire apparatus over the tissue surface.

In still further exemplary embodiments of the present invention, a low-pressure conduit can be provided in communication with the distal ends of the hollow coring needles. The low pressure can create a suction in the needles to facilitate insertion of the coring needles into tissue and/or removal of cut tissue portions from the lumen of the needles. A filter arrangement can optionally be provided to capture the tissue portions extracted from the needles during operation. Such a low-pressure or suction arrangement can be provided in combination with any of the exemplary devices described above that are adapted to remove portions of tissue by insertion and withdrawal of one or more coring needles.

Further exemplary embodiments of the present invention can provide a cosmetic method that can improve the appearance of skin by mechanical generation of fractional damage in the tissue. Such damage can be generated by removal of small portions of tissue to generate small holes in the tissue, e.g., less than about 1 mm in width or diameter, e.g., less than about 800 microns wide, or about 500 microns or less in width, for example, between about 300 and 500 microns in width. The depth of the holes can be selected based on the tissue type and location being treated. For example, hole depths of about 2-5 mm can be used in skin tissue, where such depths correspond approximately to the thickness of the dermis layer. Such exemplary hole depths in skin can correspond to removal of tissue portions extending through the entire dermis and up to and/or including the subcutaneous fat layer. Shorter and/or longer needles can also be used. The holes can be formed by repeated insertion and withdrawal of one or more coring needles from the tissue as described above. The insertions and withdrawals can be performed using a manual device containing one or more coring needles, or by using a device that contains one or more needles coupled to a reciprocating arrangement. A predetermined areal fraction of removed tissue can be obtained by inserting and withdrawing an apparatus containing a particular number of coring needles, each having a particular inside diameter of a central lumen, for a particular number of times over a specified target region to be treated.

In further exemplary embodiments of the present invention, methods and apparatuses can be provided for generating a plurality of small holes in tissue by inserting and withdrawing a plurality of needles, where at least two of the needles have a different width or diameter, length, shape, and/or other geometric characteristic. For example, one or more needles can be hollow, and one or more needles can be solid with protrusions on an outer surface near the distal end. Various combinations of needle sizes, shapes, spacings, spatial arrangements, and geometries can be used in further exemplary embodiments.

The herein described embodiments pertain to a cosmetic method and apparatus. It shall further be noted that the herein described cosmetic method has been tested, and is a safe and routine procedure that can be practiced in beauty parlors or other settings. The presented method is a minimally-invasive a method. Moreover, the exemplary method can be safe as it does not present a substantial health risk, and does not require professional medical expertise to be performed. For example, no clinician is needed to perform the embodiments of the method described herein, and no risk, much less a health risk, is presented for a person being treated with said cosmetic method if standard cleanliness and sterilization procedures are employed, as will become clear from the following description.

Synergetic effects can arise from different combinations of the features and embodiments described herein, although all such combinations might not be described in detail. Further, it shall be noted that all embodiments of the present invention concerning the exemplary method, can be carried out with the order of the steps as described, nevertheless this has not to be the only and essential order of the steps and/or procedures of the exemplary method. All different orders and combinations of the method steps and/or procedures are herewith described.

These and other objects, features and advantages of the present invention will become apparent upon reading the following detailed description of exemplary embodiments of the present invention, when taken in conjunction with the appended drawings and claims.

BRIEF DESCRIPTION OF THE DRAWINGS

Further objects, features and advantages of the present invention will become apparent from the following detailed description taken in conjunction with the accompanying figures showing illustrative embodiments, results and/or features of the exemplary embodiments of the present invention, in which:

FIG. 5E is a side cross-sectional view of a distal portion of a fifth coring needle that can be used in accordance with exemplary embodiments of the present invention;

FIG. 6 is a schematic side view of a fourth apparatus for mechanically generating fractional damage in tissue that includes a low-pressure conduit in accordance with further exemplary embodiments of the present invention;

FIG. 7 is an exemplary set of surface images taken at various times showing the appearance of fractional damage generated in porcine skin using various needle types;

FIG. 8 is an exemplary set of cross-sectional, histologic images stained with masson's trichrome and taken at various times showing the appearance of fractional damage generated in porcine skin using a coring needle as compared to an undamaged control site;

Figures 1A, 1B:
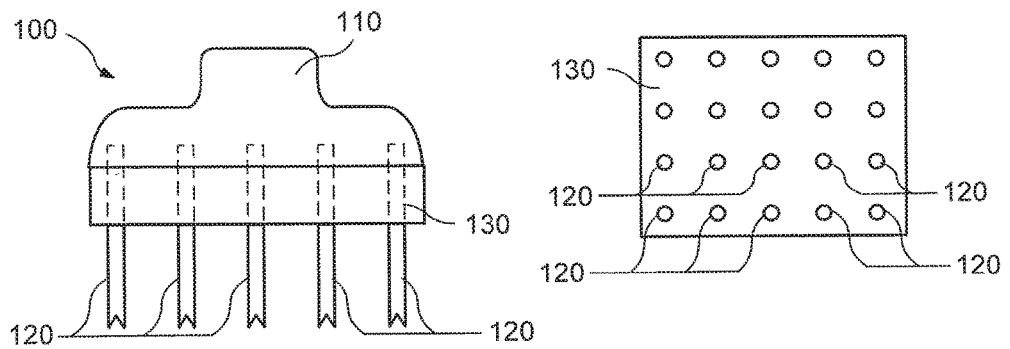
FIG. 1A is a schematic side view of a first apparatus for mechanically generating fractional damage in tissue in accordance with exemplary embodiments of the present invention.
FIG. 1B is a bottom view of the exemplary apparatus shown in FIG. 1A.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present invention will now be described in detail with reference to the figures, it is done so in connection with the illustrative embodiments and is not limited by the particular embodiments illustrated in the figures. It is intended that changes and modifications can be made to the described embodiments without departing from the true scope and spirit of the exemplary embodiments of the present invention as defined by the appended claims.

DETAILED DESCRIPTION OF EXEMPLARY EMBODIMENTS

Exemplary embodiments of the present invention relate to and are directed to method and apparatus for generating fractional damage in tissue such as, but not limited to, skin tissue. A side view of an exemplary apparatus 100 for generating fractional damage in tissue is shown in FIG. 1A. This exemplary apparatus 100 can include one or more needles 120, where the needles 120 are configured to remove small portions of tissue when they are inserted into and then withdrawn from the tissue. For example, the needles 120 can be hollow, e.g., such that they include a lumen therein. The apparatus can optionally include a substrate 130, with the one or more needles 120 affixed or coupled to the substrate 130. Although the substrate 130 is illustrated in FIG. 1A, certain exemplary embodiments of the present invention can be provided that do not include such substrate 130. The substrate 130 can provide mechanical stability to the one or more needles 120 and/or facilitate their positioning and manipulation. An optional handle 110 can be affixed to the substrate 130 or formed as a part thereof. The substrate 130 can have a substantially flat lower surface from which the needles 120 protrude, or this surface can be curved or otherwise contoured, e.g., to more closely match a contour of the tissue surface. The substrate can optionally be formed as part of a housing, or affixed to such housing, for example, where a portion of such housing may be shaped to form the handle 110.

A bottom view of the exemplary apparatus 100 is shown in FIG. 1B. The exemplary needles 120 can be arranged in a square or rectangular pattern, as shown in FIG. 1B. Alternatively, the rows of needles 120 can be offset or staggered, e.g., to form a triangular or hexagonal pattern or the like. Other exemplary arrangements of the needles 120 can also be used, such as a random distribution of the needles 120 on the substrate 130.

Figures 2A, 2B:
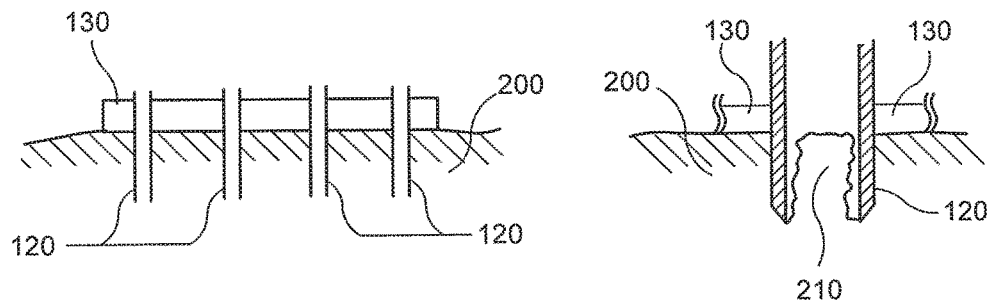
FIG. 2A is a schematic side view of the exemplary apparatus shown in FIG. 1A being applied to a biological tissue.
FIG. 2B is a schematic side view of a tissue portion being removed using the exemplary apparatus shown in FIG. 1A.
Figure 2C:
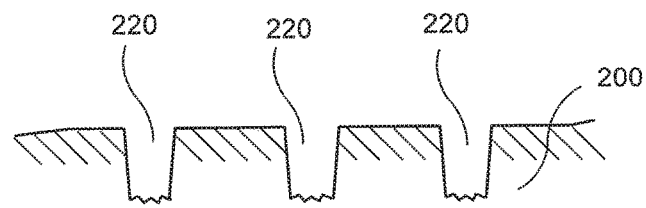
FIG. 2C is a schematic side view of a plurality of holes formed in the biological tissue using the exemplary apparatus shown in FIG. 1A.

The exemplary apparatus 100 can be pressed onto a tissue surface, such that the needles 120 penetrate into the tissue 200, as shown in FIG. 2A. A plug 210 of tissue that has been separated from the surrounding tissue 200 by the hollow needle 120 and located at least partially within the lumen of the needle 120 is shown in FIG. 2B. Such exemplary plugs 210 can be removed from the surrounding tissue 200 when the needles 120 are withdrawn from the tissue 200 to form a plurality of holes 220, as shown in FIG. 2C. For example, the exemplary apparatus 100 can be used as a stamping tool, where the plurality of needles 120 can be inserted into the tissue 200 once or a plurality of times in different locations. This exemplary "coring" procedure can facilitate a formation of a plurality of the holes 220 in the tissue 200. The holes 220, which can be made during each insertion and withdrawal sequence, can have a spacing substantially similar to the spacing of the coring needles 120 in the apparatus 100.

The discrete holes 220 formed by the exemplary apparatus 100 can produce regions or areas of a damaged skin tissue that can elucidate a healing response, which can be similar to the effects produced using conventional fractional resurfacing techniques and systems. The size of the holes 220 can be determined by the size of the needles 120. For example, the diameter of the holes 220 can correspond approximately to an inside diameter or lumen width of the needles 120, although the observed hole diameter can be somewhat smaller after formation due to factors such as, e.g., the malleable/elastic nature of the tissue, a tendency for the gaps in the tissue to close and/or the hole wall to partially adhere to itself, and mechanical forces applied to the tissue before or during a formation of the holes 220. Accordingly, the diameter (size) of a hole 220 formed can generally be defined as the inner diameter of a hollow coring needle 120 that is used to form the hole 220 by cutting and removing a portion 210 of the tissue.

According to an exemplary embodiment of the present invention, the diameter or width of the holes or damaged tissue regions can be less than about 1 mm, e.g., about 0.8 mm or less, which can be well-tolerated by the skin. In further exemplary embodiments, the hole diameter can be about 0.5 mm or less, which may be better-tolerated and result in a faster healing response. For example, the holes formed can be between about 0.3 mm and 0.5 mm (i.e., between 300 and 500 microns).

In certain exemplary embodiments of the present invention, the coring needle 120 can be formed, e.g., from a conventional syringe needle or an equivalent tube having a size between 18 and 30 gauge, which corresponds approximately to internal diameters and hole sizes between about 0.84 mm and 0.14 mm. Exemplary needle sizes between about 22 and 25 gauge (e.g., internal diameters and corresponding hole sizes between about 0.40 mm and 0.24 mm) can be used, because such needle sizes can produce holes that are small enough to be particularly well-tolerated with a needle large enough to be mechanically stable and reliable when repeatedly inserted into and withdrawn from the skin. Larger gauges (and smaller diameters) of coring needles 120, e.g., greater than 30 gauge, can be used in certain exemplary embodiments, even though such needles may exhibit increased flexing and/or mechanical weakness when repeatedly inserted into and withdrawn from the tissue 200, and may also be prone to clogging. Larger needles 120 that can form correspondingly larger-sized holes 220, e.g., needles 120 having a gauge smaller than 18, can also be used for certain procedures and tissues, even though they can generate more pain than smaller needles, and the larger holes 220 may not be as well-tolerated, e.g., there may be an increased likelihood of scarring, infection, or other undesirable side effects.

Exemplary sizes of the holes 220 of about 200-500 microns can generally correspond to the hole sizes formed in conventional fractional surfacing procedures, although the mechanical coring procedure described herein does not generate any thermal damage at the boundaries of the removed tissue portions 210. These hole sizes appear to be well-tolerated in the skin tissue, with smaller holes generally being better tolerated (e.g., associated with faster healing times), and larger holes providing more extensive damage that can stimulate a stronger response in the tissue. The exemplary apparatus 100 can be configured to form the holes 220 having similar dimensions. Larger or smaller holes can be formed in certain tissues to achieve particular healing responses or other physical or biological responses.

The surface or areal fraction of the tissue damage can be determined (for a single insertion and withdrawal of the apparatus 100) by the diameters and spacings of the needles 120 provided on the substrate 130. The areal fraction of damage can be increased in a particular target region of tissue by applying the exemplary apparatus 100 to a plurality of locations in the target area. For example, the fraction of tissue surface covered by the holes 220 following an exemplary treatment procedure of a target area can be as small as about 0.1 (10% fractional removal) and as large as about 0.7 (i.e., 70% fractional removal). In general, areal fractions of holes can be between about 0.2 and 0.5, or between about 0.2 and 0.4. These areal coverage values may be preferable for some procedures because they can be better tolerated, may lead to shorter local healing times, etc. Smaller or larger areal coverages can also be generated in certain tissues, e.g., to provide a desired healing response or the like in the tissue.

The number of coring needles 120 provided in a substrate 130 and their spacing can be selected based on several considerations. For example, a larger number of the needles 120 can produce a larger areal fraction of damage each time the exemplary apparatus 100 is inserted into and withdrawn from the tissue. This can facilitate faster treatment of a target area by requiring fewer insertion/withdrawal cycles for a particular final areal coverage. However, providing a very large number of the needles 120 in a substrate 130 can be expensive and/or present manufacturing challenges. Further, a larger force is needed to simultaneously insert a large number of the needles 120 simultaneously into a tissue as compared to a substrate 130 of the same dimensions containing a smaller number of needles. Accordingly, the number of the needles 120 in the exemplary apparatus 100 can be between about 3 and 25, or between about 6 and 20. In certain embodiments of the present invention, larger or smaller numbers of the needles 120 can be provided for generating fractional damage in particular tissues and/or for treating larger areas with fewer insertion and withdrawal cycles.

Distances between adjacent ones of the needles 120 can be less than about 15 mm, e.g. about 10 mm or less, or even about 5 mm or less. Smaller spacings can generate a larger fractional area of damage over a smaller area based on a single insertion of the plurality of needles 120 into the tissue. Larger separation distances (e.g. greater than about 20 mm) can lead to large numbers of insertion/withdrawal cycles to generate a particular areal coverage of holes 220 in the tissue being treated. Such large spacings between needles may also not be suitable for treating relatively small target areas, e.g., having a width of about 1 inch or less. Alternatively, very small separation distances between the coring needles 120 (e.g., on the order of 3 mm or less) can be used, although such small needle spacings may present manufacturing difficulties. It may also be more difficult to achieve a fairly uniform surface distribution of holes 220 over larger target areas using the exemplary apparatus 100 having needles 120 that are very closely spaced. In general, the number of the needles 120 and spacings between such needles 120 provided in any exemplary apparatus described herein can be selected based on such factors as the size and structure of the target regions to be treated, the desired surface coverage, speed of the procedure (e.g., more needles 120 can facilitate fewer insertion/withdrawal cycles to achieve a particular surface coverage), etc.

The exemplary depth of the holes 220 formed in the tissue can correspond approximately to the length of the needles 120 protruding from a lower surface of the substrate 130. For example, the needles 120 can extend about 2-5 mm below the lower surface of the substrate 130. In skin tissue, such coring needle protrusion lengths can facilitate the formation of the holes 220 that extend through substantially the entire thickness of the dermal layer without penetrating significantly into the underlying subcutaneous fat layer. A penetration of the needles 120 through substantially the entire dermal thickness can facilitate removal of the tissue portions 210, which can include mostly dermal tissue that can be more easily separated from the subcutaneous fat layer during withdrawal of the needles 120. In other exemplary embodiments, the needles 120 can be configured to penetrate through the dermis and some distance into the subcutaneous fat layer. In still further embodiments, the needles 120 can protrude at different lengths from the substrate 130 in an apparatus that includes a plurality of needles. A plurality of needles 120 having widths that are different from one another can also be provided in any of the multi-needle embodiments described herein, e.g., to provide a more randomized pattern of fractional damage in the tissue.

Shallower or deeper holes 220 can be formed using the needles 120 that are shorter or longer, respectively. The exemplary lengths and diameters of the needles 120, and the exemplary depths and widths of the corresponding holes 220 formed, can be selected based on the characteristics of the tissue 200 being treated and the desired effects to be achieved. Using the needles 120 having different characteristics (e.g., size, diameter, or geometry as described herein) can generate desirable cosmetic effects in different tissues.

Figure 3A:
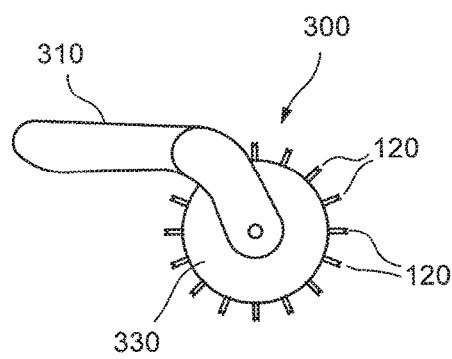
FIG. 3A is a schematic side view of a second apparatus for mechanically generating fractional damage in tissue in accordance with further exemplary embodiments of the present invention.
Figure 3B:
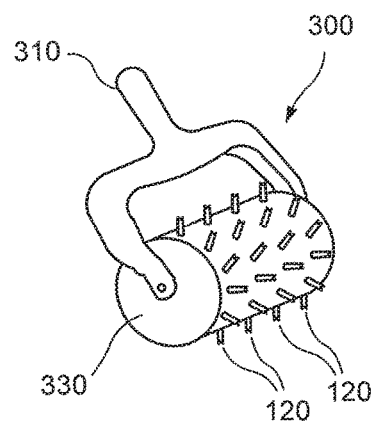
FIG. 3B is a perspective view of the exemplary apparatus shown in FIG. 3A.

A side view of a further exemplary apparatus 300 for generating fractional damage in tissue is shown in FIG. 3A. This exemplary apparatus 300 can include the plurality of hollow needles 120 affixed to a cylindrical roller 330. The roller 330 can be pivotally connected to a handle 310 such that it can rotate. A perspective view of the exemplary apparatus 300 is shown in FIG. 3B. The needles 120 can be arranged as a plurality of rows on the roller 330, as shown in FIG. 3B. Other arrangements of the needles 120 can also be used, such as staggered rows or a random distribution of the needles 120 on the roller 330.

The exemplary apparatus 300 can be pressed onto a tissue surface, such that one or more of the needles 120 penetrates into the tissue 200. The apparatus 300 can then be traversed over a region of tissue to be treated such that the needles 120 are forced into and then withdrawn from the tissue 200 as the roller 330 rolls over the tissue surface. The exemplary apparatus 300 illustrated in FIGS. 3A and 3B is not necessarily drawn to scale. For example, the protrusion lengths of the needles 120 from the roller 330 may be smaller as compared to the diameter of the roller 330 than illustrated in these figures.

Figure 4A:
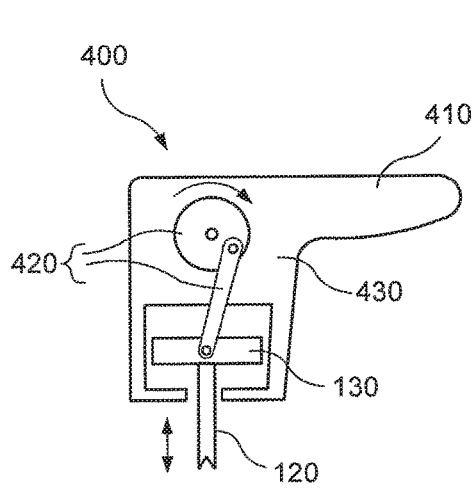
FIG. 4A is a schematic side view of a third apparatus for mechanically generating fractional damage in tissue in accordance with further exemplary embodiments of the present invention.

A further exemplary apparatus 400 in accordance with exemplary embodiments of the present invention is shown in FIG. 4A. The exemplary apparatus 400 can include one or more of the coring needles 120 affixed to a substrate 130, which can then be mechanically coupled to a reciprocating arrangement 420 provided within a housing 430. The housing 430 can also include a handle 410 to facilitate a manipulation of the exemplary apparatus 400. The reciprocating arrangement 420 can be configured to displace the needle 120 back and forth along a direction that can be substantially parallel to the axis of the needle 120. For example, the reciprocating arrangement 420 can be powered and/or actuated by a motor or the like, controlled by a switch that can turn the reciprocating arrangement 420 on and off, and/or further control the reciprocating frequency and/or protrusion distance of the needle 120 below the lower surface of the housing 430. In a further exemplary embodiment, the needles 120 can protrude a particular distance from the lower surface of substrate 130, and the reciprocating arrangement 420 can be configured to extend and withdraw the substrate to and from a position where the lower surface of the substrate 130 is substantially flush with at least a portion of the lower surface of the housing 430. In such exemplary embodiment, the protrusion distance of the needles 120 can determine the depth of the holes 220 formed, rather than the cyclical position of the substrate 130 relative to the housing 430.

Figure 4B:
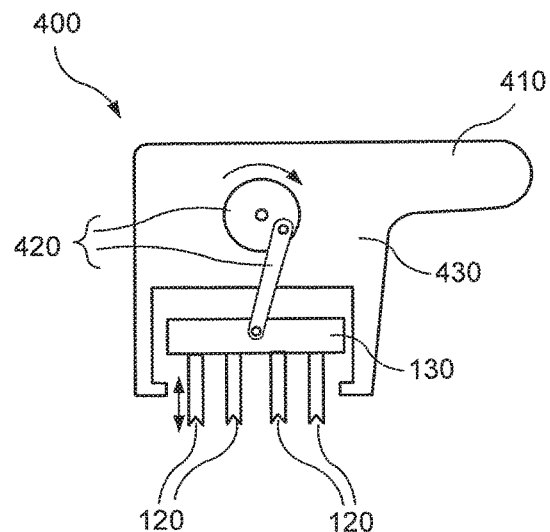
FIG. 4B is a schematic side view of the third apparatus shown in FIG. 4A that is provided with a plurality of coring needles in accordance with further exemplary embodiments of the present invention.

Another exemplary embodiment of the apparatus 400 is illustrated in FIG. 4B. In this exemplary embodiment, the needles 120 are shown affixed to the substrate 130. The various parameters, geometries, and characteristics of the needles 120 and the substrate 130 described herein and/or illustrated in the figures can be used, individually or in combination, with the exemplary apparatus 400 illustrated in FIG. 4B.

The exemplary apparatus 400 of FIGS. 4A and 4B can be traversed over a region of tissue to be treated such that the one or more needles 120 forms a plurality of the holes 220 in the tissue 200 as described herein. The exemplary depth of the holes 220 can be determined by the configuration of the reciprocating arrangement 420, the protrusion lengths of the needles 120, and/or the characteristics of the substrate 130, as described herein. The spacing of such holes 220 in the tissue can be determined, e.g., by the reciprocating frequency and/or the translational speed of the apparatus 400 over the tissue surface, and the spacings between the needles 120 if a plurality of such needles 120 are provided, as shown in FIG. 4B. For example, the exemplary apparatus 400 can include a speed and/or position sensing arrangement that can be provided in communication with the reciprocating arrangement 420 to generate a particular spacing and/or areal fraction of the holes 220.

In further exemplary embodiments, the housing 430 can be configured to stretch skin or other tissue when the exemplary apparatus 400 is placed on the tissue to be treated. Such exemplary stretching can facilitate mechanical stabilization of the tissue, e.g., such that the one or more needles 120 can more easily be inserted and/or withdrawn from the tissue, while reducing or avoiding deformation of the tissue area being treated. Such stretching of the tissue 200 can also reduce the effective size of the holes 220 or other regions of damage formed by the apparatus when the tissue is allowed to relax after treatment. Alternatively or in addition, the surface of the region of skin or tissue to be treated can be stretched or stabilized using other techniques prior to and/or during treatment of the region in accordance with any of the exemplary embodiments described herein.

In another exemplary embodiment, the reciprocating arrangement 420 can further include a translational mechanism configured to translate the one or more of the needles 120 over the surface of the tissue 200 in one or two orthogonal directions or a combination thereof. For example, the reciprocating arrangement 420 can be configured to translate such one or more of the needles 120 over a portion of the tissue surface, while the exemplary apparatus 400 is held stationary with respect to the tissue surface. In one exemplary embodiment, the reciprocating arrangement 420 can be configured to translate the one or more needles 120 along a single direction to form one or more rows of the holes 220 or damaged regions. The exemplary apparatus 400 can optionally be translated over the tissue surface after such rows are formed to generate a plurality of such holes 220 over a larger region of the tissue.

In further exemplary embodiments of the present invention, any of the exemplary apparatuses described herein can be configured to generate the holes 220 in any of a variety of spatial distributions in the tissue being treated. For example, the holes 220 can be formed as one or more rows, a regular two-dimensional pattern (such as a square, rectangular, or triangular array), a random distribution, or the like. Such patterns or spatial distributions of holes 220 can be generated based on, e.g., the exemplary configuration of one or more of the provided needles 120 in the substrate 130, the properties of the reciprocating arrangement 420, and/or the rate of translation of the exemplary apparatus 400 over the surface of the tissue 200.

A cross-sectional side view of a distal portion of an exemplary needle 120 is shown in FIG. 5. The distal end 500 of the needle 120 can be provided with a sharpened edge to facilitate penetration of the needle 120 into the tissue 200 being treated. One or more protrusions 510 can optionally be provided within the lumen, e.g., along an inner surface of the needle 120. Such protrusions 510 can facilitate a removal of the tissue plugs 210 that can be present within the needle 120 when it is inserted into the tissue 200 as described herein. For example, such protrusions 510 can be angled upward as shown in FIG. 5 to facilitate the needle 120 to penetrate the tissue 200 easily. These protrusions 510 can then grab onto the tissue plug 210 in a barb-like manner to pull the plug 210 from the surrounding tissue 200 when the needle 120 is withdrawn. The plugs 210 that are removed and reside within the needle 120 can be pushed upward towards the proximal end of the needle 120 by subsequent plugs 210 formed by successive insertions of the needle 120 into the tissue 200.

Figure 5A:
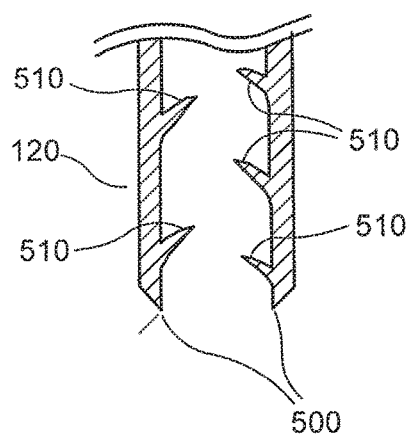
FIG. 5A is a cross-sectional side view of a distal portion of a first needle that can be used in accordance with exemplary embodiments of the present invention.
Figure 5B:
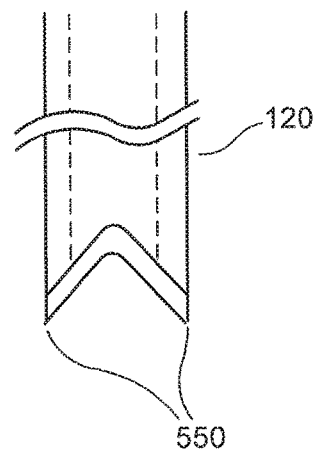
FIG. 5B is a side view of a distal portion of a second needle that can be used in accordance with exemplary embodiments of the present invention.

Another exemplary configuration for the distal end of a coring needle 120 is shown in FIG. 5B. The distal end of the needle 120 can be provided with a single point or prong 550, similar to that of a conventional Chiba needle, or with two or more points or prongs 550, e.g., in a configuration similar to that of the outer cannula of a conventional Franseen needle or crown-point tip. For example, such prongs 550 can be formed by a planar grinding of the end portion of a hollow tube at acute angles relative to the longitudinal axis of the tube, at one or more angular intervals around the longitudinal axis. For example, a 2-pronged needle end, such as illustrated in FIG. 5B, can be formed by grinding the opposite sides of a hollow tube or needle (e.g., orientations that are 180 degrees apart) in a plane that forms an acute angle with the longitudinal axis of the tube. Similarly, a 3-pronged needle can be formed by angular grinding of the needle at 120 degree intervals; 4-pronged needles can be formed by grinding at 90 degree intervals, etc. Such prongs 550 can facilitate the insertion of the needle 120 into the tissue 200, and can further facilitate detachment and removal of tissue portions 210 upon the withdrawal of the needle 120 from the tissue 200.

Figure 5C:
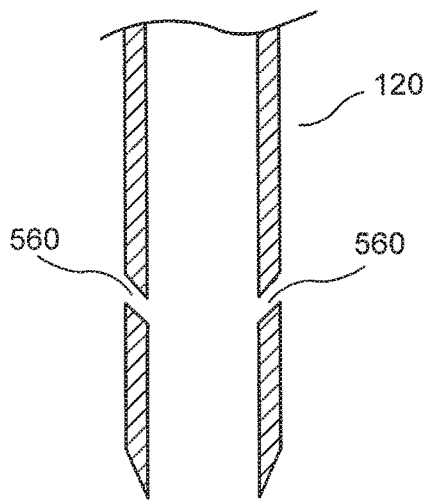
FIG. 5C is a side cross-sectional view of a distal portion of a third coring needle that can be used in accordance with exemplary embodiments of the present invention.

Other exemplary configurations of one or more of the needles 120 can be used with any of the various exemplary embodiments described herein. For example, another needle 120 as shown in a cross-section in FIG. 5C can be used, which includes one or more angled notches 560 provided in the needle walls, e.g., near the distal end of the needle 120. Such exemplary notches 560 can extend partially or completely through a wall of the exemplary hollow needle 120. During the insertion and/or withdrawal of the needle 120, such notches 560 can be adapted to cut into the tissue adjacent to the needle 120, thereby removing a portion of the tissue and generating a hole or gap. For example, the notches 560 can be angled upward (as shown in FIG. 5C) and/or downward relative to the distal end of the needle 120.

Figure 5D:
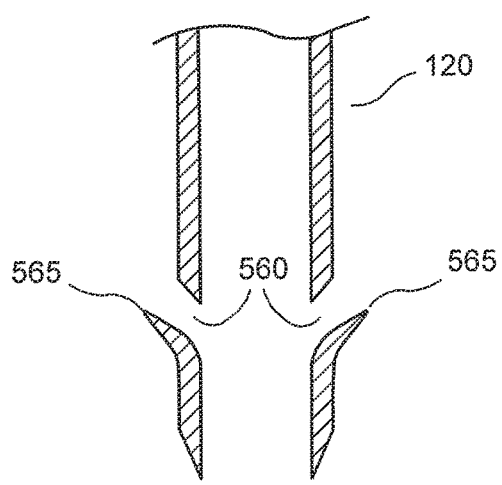
FIG. 5D is a side cross-sectional view of a distal portion of a fourth coring needle that can be used in accordance with exemplary embodiments of the present invention.

In further exemplary embodiments, an edge 565 of the notches 560 can optionally protrude from the outer periphery of the needle wall, as shown in cross section in FIG. 5D. The protruding edge 565 can provide a cutting edge or the like, which may be viewed as analogous to the configuration and operation of some cheese graters but on a smaller scale, to facilitate separation and removal of a portion of the tissue proximal to the needle 120 as it is moved through the tissue.

In further exemplary embodiments, one or more of the needles 120 can be provided as a solid non-hollow needle 520 that includes one or more extensions 570 protruding from a lateral side thereof, e.g., as shown in an exemplary cross-sectional view in FIG. 5E. If more than one such extension 570 is provided, they can be distributed at various angular intervals around the axis of the needle 520. The extensions 570 can extend over any one of various lengths along the axis of the solid needle 520, and can be located near the distal end of the needle 520. These extensions 570 can be provided with a size and shape that is structured or adapted to remove small portions of tissue when the needle 520 is inserted into and/or withdrawn from the tissue being treated. For example, the extensions 570 can be similar in shape to the protrusions 510 shown in FIG. 5A, with the extensions 570 provided on an outer surface of the solid needle 520 rather than on an inner surface of a hollow needle 120 as shown in FIG. 5A. Preferably, the outer diameter of the extensions 570 around the longitudinal axis of the needle 520 can be less than about 1 mm, and optionally less than about 0.5 mm. Such small sizes can limit the size of the damaged regions of tissue generated, and thereby reduce or prevent formation of visible markings or scars in the damaged tissue.

The exemplary illustrations of the needles 120, 520 shown in FIGS. 5A-5E are not necessarily drawn to scale. For example, the sizes of a protrusion 510, a notch 560, and/or an extension 570 relative to the needle width or diameter, and/or their distances from the needle tip, can vary from what is shown in the illustrations. The specific shapes of these features and, e.g., the notch edges 565, can also vary from those shown in the drawings. Further, different ones of the needles 120, 520 can be provided with different diameters, feature sizes, and or lengths in a single apparatus 100, 200, 400, 600.

In still further exemplary embodiments, one or more extensions 570 can be provided on an outer wall or surface of any of the hollow coring needles 120 described herein. In yet further exemplary embodiments, a single exemplary apparatus 100, 300, 400, 600 can be provided with a plurality of needles 120, 520, where one or more of such needles 120, 520 can be provided with different ones of the features illustrated in FIGS. 5A-5E and described herein.

In further exemplary embodiments of the present invention, the exemplary apparatus 100, 300, 400 can be provided with suction or low pressure to improve the ease of needle insertion and facilitate removal of tissue portions 210 from the needle upon withdrawal from the tissue 200. An exemplary apparatus 600 that includes one or more coring needles 120, a substrate 130, and a low-pressure conduit 620 is illustrated in FIG. 6. The conduit 620 is provided in communication with a proximal end of the coring needles 620. The conduit 620 can also be connected to a source of low pressure (not shown) such as, e.g., a vacuum pump, a partially-evacuated vessel or container, a piston, another vacuum source, or the like. The low pressure in the conduit 620 can generate a suction in the needles 120, which can facilitate insertion of the needles 120 into tissue 200 being treated, extraction of tissue portions 210 from the surrounding tissue 200, and/or removal of such tissue portions 210 from the lumen of the needles 120 after the needles 120 are withdrawn from the tissue 200.

The exemplary apparatus 600 can optionally include a valve, restriction, and/or other pressure arrangement between the low pressure source and the proximal ends of the needles 120, where the pressure arrangement is adapted to control the degree of suction or low pressure present in the conduit. In an alternative exemplary embodiment, characteristics of the low pressure source can be controlled directly to vary the pressure in the conduit 620.

An optional filter arrangement 630 can be provided in the exemplary apparatus 600, e.g., between the proximal end of the needles 120 and the low-pressure source. For example, the filter arrangement 630 can be provided at a location in the conduit 620 as illustrated in FIG. 6. The filter arrangement 630 can include a polymer or metal mesh or screen, a paper filter, or the like adapted to capture tissue portions 210 that may be sucked out of the needles 120 during operation of the apparatus 600. The filter arrangement 630 can include a filter element that can be easily cleaned or discarded during or after operation of the exemplary apparatus 600. The filter arrangement 630 is preferably sized so that it will not become clogged with captured tissue portions 210 during operation, which may reduce or eliminate the suction provided to the needles 120. An optional reservoir or container (not shown) can be provided and adapted to store tissue portions 210 that are trapped by the filter arrangement 630, where such tissue portions 210 can be directed into the container or fall into it under the influence of gravity, and can then be removed from the exemplary apparatus 600 and discarded.

The low-pressure conduit 620 and optional filter arrangement 630 as described above can be combined with any of the exemplary embodiments described herein, including the exemplary devices 100, 400 shown in FIGS. 1 and 4. The advantages of such a combination can include, e.g., easier insertion of the needles 120 into tissue 200 being treated, more effective removal of tissue portions 210 from the central lumen of needles 120 during operation of the devices, reduced clogging of the needles 120, etc.

In further exemplary embodiments of the present invention, a method is provided that allows for the removal of small portions of aged or damaged skin, which can facilitate and/or promote the growth of new skin components while reducing or avoiding undesirable side effects such as scarring, infection, and the like.

Further exemplary embodiments of the present invention provide a cosmetic method that can improve the appearance of skin by mechanical generation of fractional damage in the tissue. Such damage can be generated by removal of portions of tissue to generate small holes in the tissue. A width or diameter of these holes can be, e.g., less than about 1 mm, or less than about 0.5 mm, e.g., between about 0.3 mm and about 0.5 mm, as described herein above.

The depth of the holes can be selected based on the tissue type and location being treated. For example, hole depths of about 2-5 mm can be used in skin tissue, where such depths correspond approximately to the thickness of the dermis layer. Such hole depths in skin can correspond to removal of tissue portions extending through the entire dermis and up to the subcutaneous fat layer. In further exemplary embodiments, longer needles 120, 520 can be provided that can extend into the subcutaneous fat layer when inserted partially or fully into skin tissue.

Tissue portions can be removed, and holes can be formed, by repeated insertion and withdrawal of one or more needles 120, 520 from the tissue as described herein above. The insertions and withdrawals can be performed using a manual device containing one or more needles 120, 520, or alternatively by using a device that contains one or more needles 120, 520 coupled to a reciprocating arrangement 420. A predetermined areal fraction of removed tissue can be obtained by inserting and withdrawing a particular number of needles 120, 520 for a particular number of times over a specified target region to be treated.

In further exemplary embodiments of the present invention, a source of pressurized fluid, e.g. saline or the like, can be coupled to the lumen of the hollow coring needle 120. The flow of such fluid can be controlled using conventional means, and used to clean or flush out tissue portions and/or other debris that may be present in the lumen. In still further embodiments, a heat source, e.g., a resistive heater or current, can be provided in communication with one or more of the needles 120, 520, and adapted to cauterize, ablate, or otherwise remove tissue or other residue that may adhere to the needles 120, 520.

As suggested by the observations described below, the method of mechanically generating fractional damage in skin tissue by removing small tissue portions, e.g., by repeatedly inserting and withdrawing one or more coring needles, appears to be safe and well-tolerated by the skin, with little risk of infection or unwanted side effects as compared with laser-based resurfacing procedures. Such methods can stimulate collagen formation in skin and lead to an increase in dermal and epidermal thickness, which can improve the appearance of aged or photo-damaged skin.

Example

A large-animal study of the method and apparatus according to certain exemplary embodiments of the present invention was performed. Tissue coring needles were produced by modifying conventional hypodermic needles, so that a cylindrical area of tissue is removed when they puncture the skin and are then withdrawn, similar to a core biopsy but on a smaller size scale. Standard 25 gauge hypodermic needles (e.g., Becton Dickinson, Franklin Lakes, N.J.), having a 260 micron inner diameter, were ground down such that their anti-beveled edges were removed, to form hollow needles having a double-crown or double-pronged tip, such as that illustrated in FIG. 5B. Devices were prepared in accordance with embodiments of the present invention that include four such coring needles affixed in a 2×2×4 cm block of rubber. The needles were provided in a square array, with 8 mm of separation between the needles along the sides of the square, and with the distal ends of the needles extending 4 mm from the lower surface of the rubber block. For comparison, several similar 4-needle devices were prepared using different types of needles. Devices were assembled with four standard or "regular" 25 gauge hypodermic needles (not having double-pronged ground tips), four regular 23 gauge needles, four "solid" 25 gauge needles (having the same outer diameter but without a hollow center) and four 23 gauge coring (double-pronged) needles. These additional devices were also tested as described herein.

One female miniature swine (*Sus scofa domesticus*), 1½ years of age and weighing 117 kg, was utilized for this study. The pig was subjected to general anesthesia and positioned on its right side. The hair from the left flank was clipped and the skin was prepped with soap. The pig was given a single dose of buprenorphine (0.01 mg/kg) for analgesia, and then draped in a sterile fashion.

Using a template, the corners of 32 1-inch treatment squares were marked by tattoo. A total of 24 squares were treated with the devices containing either standard ("regular") 25 gauge hypodermic needles, solid 25 gauge needles, or 23 or 25 gauge coring needles. The device used for each treatment square was repeatedly pressed onto the square of skin tissue by hand and removed for a prescribed number of times, with the device being randomly translated within the area of the square being treated before each re-insertion. The number of insertions/removals for each site was calculated to provide an areal fraction of affected tissue (based on the ID of the needles) of either 0.20 (20% coverage) or 0.40 (40% coverage). For example, a coverage of 20% corresponds to about 625 insertion/withdrawal cycles per square inch with a device containing four 25 gauge needles, and a coverage of 40% corresponds to about 1250 insertion/withdrawal cycles of the same device per square inch. Coverages of 20% and 40% can also be achieved with about 362 and 724 insertion/withdrawal cycles per square inch, respectively, of a device having four 23 gauge needles. Eight marked squares were left untreated as controls. Devices containing new needles were used for each treatment site.

At the completion of the coring procedure, 4 mm punch biopsies were obtained from each treatment and control site. These biopsy sites were then each closed with a single, 3-0 nylon suture. The wounds were then dressed with triple antibiotic ointment, zeroform, gauze and tape.

This entire procedure was then repeated on the opposite (right) flank, and photographs were taken of the treatment and control squares on this side both before and after the needle devices were applied to the various treatment sites. On days 7, 28, 56, and 84 (1, 4, 8, and 12 weeks, respectively) after the initial coring procedures were performed, the pig was again placed under general anesthesia and further biopsies from sites on the left flank, and pictures of the sites on the right flank, were taken.

Four series of photographs of certain treatment squares of pig skin tissue are presented in FIG. 7. Pictures in row A were taken of a control square that was not penetrated by any needles; pictures in row B were taken of a control square treated with regular (conventional) 25 gauge hypodermic needles; pictures in row C were taken of a control square treated with solid 25 gauge needles; and pictures in row D were taken of a control square treated with 25 gauge coring needles having 2-prong tips configured to remove a portion of the tissue upon being withdrawn. Pictures in the first and second columns of FIG. 7 were taken immediately pre- and post-needle treatment. Pictures in the third, fourth, and fifth columns of FIG. 7 were taken at 1, 4, and 12 weeks after the needle treatment, respectively. These photographs were taken using a Nikon D3100 digital SLR with a Nikkon Micro-Nikkor 105 mm Macro Lens (Nikon Corporation, Tokyo, Japan). Image measurements were made using Adobe Photoshop CS4 (Adobe Systems Incorporated, San Jose, Calif.). The surface coverage for each treated square shown in FIG. 7 was about 20%.

The micro-coring needle apparatus and technique in accordance with embodiments of the present invention appeared to be well-tolerated. All treatment areas were observed immediately post-treatment to be characterized by redness and serous exudates (second column of FIG. 7). This initial appearance is similar to that observed with some laser resurfacing procedures. However, the treated sites healed quickly, with any observable erythema resolved within two weeks of the treatment. By 4 weeks (fourth column in FIG. 7), the treatment sites appeared to be completely healed. The sites treated with solid needles at 40% coverage appeared to be the last to heal. There was no evidence of infection or scarring at any of the 64 treatment sites over the 12-week study.

Punch biopsies from the treated sites were fixed with 10% formalin, embedded in paraffin and cut into 5 μm sections. The sections were stained with hematoxylin and eosin, Masson's Trichrome, and Verhoeff-Van Gieson. Images of the sectioned and stained biopsies were acquired on a Nikon Eclipse E600 microscope in brightfield (Nikon). A series of four biopsy images with Masson's Trichrome staining for an untreated control site, taken at 0, 1, 4, and 8 weeks after treatment of the other sites are show in FIGS. 8A-8D. The images in FIGS. 8E-8H were taken of stained biopsies from a site treated with 25 gauge coring needles, as described above, at these same time intervals of 0, 1, 4, and 8 weeks after treatment of the site. The length of the scale bar in these images is 100 microns.

Histologically, the areas of tissue coring/removal after treatment with the coring needles were easily detectable and were approximately 200-300 microns in diameters and about 600-700 microns in depth. (See FIG. 8E.) All of the treatment sites exhibited re-epithelialization by one week of elapsed time after treatment, as shown in FIG. 8F. The coring sites exhibited enhanced undulating rete ridges, which increases the epidermal-dermal junction interface as shown in FIGS. 8F-H, as compared to the control (untreated) area shown in FIGS. 8A-D. These treated sites also had a thicker papillary dermis, most notably visible 4 weeks after treatment as shown in FIG. 8G. This region contained numerous fibroblasts, which are the cells responsible for new collagen and elastin synthesis.

After 8 or more weeks post-treatment (see FIG. 8H), the coring sites appeared to return to a more normal skin architecture, similar to the control sites shown in FIGS. 8A-D. This observation is not surprising, because the porcine skin that was treated was not aged but healthy. Further, porcine skin tissue does not exhibit human-like wrinkles, photodamage, or similar skin vasculature, so a "cosmetically" improved appearance of the pig skin would not be expected.

However, there is histologic evidence that some rejuvenation and remodeling occurred. The images shown in FIGS. 9A and 9B are the biopsy samples of an untreated control site and one treated with 25 gauge coring needles, respectively, that were stained for elastin 8 weeks after treatment. The arrows in FIG. 9B indicate a significant increase in the number and desirable orientation of elastin fibers. The length of the scale bar in FIGS. 9A and 9B is 100 microns. Elastin staining at 8 and 12 weeks after treatment of a site with coring needles revealed beading of the elastic fibers, indicating that new elastin was being laid down. These elastin fibers are newly aligned in a horizontal fashion, a configuration that has been observed after fractional laser treatment and which is thought to contribute to traction stress and skin tightening. This significant rejuvenation behavior was not observed to the same extent in control sites, nor in sites treated with the solid and regular hypodermic needle types (not shown).

Figure 9:
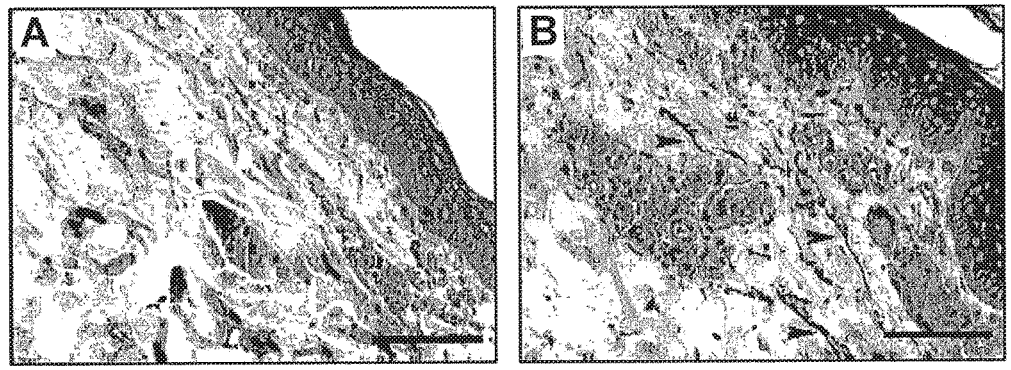
FIG. 9 is an exemplary pair of cross-sectional histologic images showing a generation of new collagen in porcine skin that was fractionally damaged using a coring needle in accordance with further exemplary embodiments of the present invention, as compared to an undamaged control site.

Whereas the significance of new, healthy fibroblast and collagen is well-documented in skin rejuvenation models, the role of elastin is less clear. Although elastin makes up a small percent of dermal connective tissue, it is clearly important, as the lack of elastin in conditions such as Ehlers-Danlos has a dramatic presentation. Studies have demonstrated objective increases in the amount of elastin after various skin rejuvenation procedures, although there is minimal correlation of this with skin tightening. It has been suggested that a horizontal realignment of elastin may lead to skin tightening rather than an increase in density. The production of new elastin in tissue sites treated with coring needles, in accordance with embodiments of the present invention, did appear to form longer and more horizontally opposed fibers as compared to the randomly distributed fibers found in the control tissues, as shown in FIG. 9.

Figure 10:
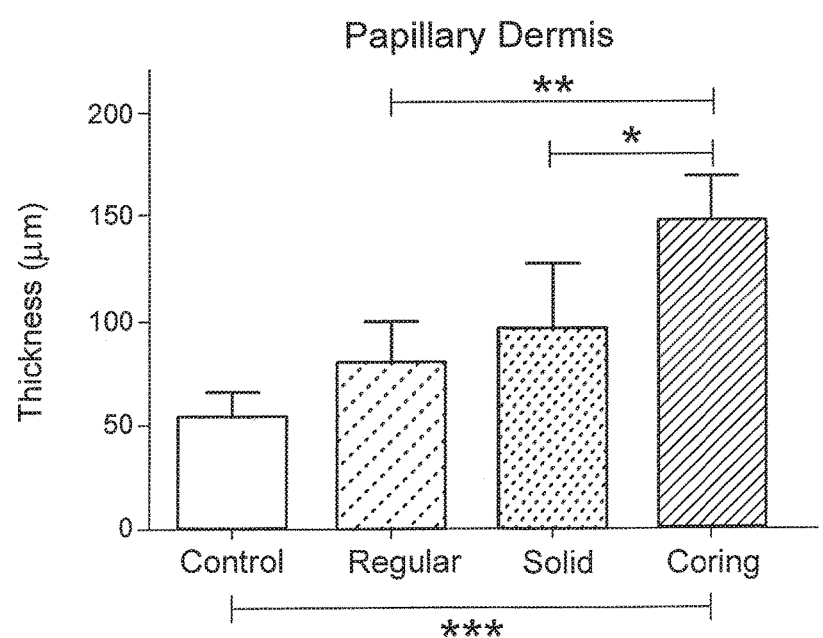
FIG. 10 is a plot of exemplary data showing the observed increase in papillary dermis thickness of porcine skin damaged with coring needles as compared to other treated and non-treated skin areas.

While all three needle types investigated (solid, regular hypodermic, and coring) appeared to induce some element of skin remodeling when compared to the untreated controls, the results of the coring needles were most profound. FIG. 10 shows a graph of measured papillary dermis thickness in biopsy samples for a control (untreated) site and for sites treated with the three types of needles, 4 weeks after treatment of the skin sites. The papillary dermis of the sites treated with coring needles was observed to be up to 196% thicker at this time as compared to the untreated control sites ($p<0.01$). Multiple group comparisons were made by ANOVA using the Tukey-Kramer post hoc analysis. A p-value of less than 0.05 was considered statistically significant. Data analysis was performed using the GraphPad Prism statistical software (GraphPad Inc, San Diego, Calif.). The vertical error bars in FIG. 10 represent a single standard deviation and (*) indicates $p<0.05$, () indicates $p<0.01$, and (*) indicates $p<0.001$, as a statistical significance level between the groups within the horizontal bars in this figure.

The observed increase in thickness of the papillary dermis in skin areas treated with coring needles may be significant with respect to cosmetic rejuvenation effects. Expansion of this zone has been correlated with treatment depth and skin contracture. For example, more aggressive resurfacing therapies (e.g., high-flux laser and dermabrasion) have been observed to result in a thicker papillary dermis at two months. Retinoic acid treatment can increase the thickness and production of collagen in the papillary dermis by 80%. The importance of the papillary dermis in skin rejuvenation may result from the specialized cells it contains. Papillary fibroblasts have been found to to be a distinct population, which are more significantly impacted by aging than their deeper, reticular conterparts. Papillary fibroblasts were observed to have a higher capacity to sustain kertinopoiesis and promote epidermal morphogenesis. It is well known that the vasculature of the papillary dermis supplies the epidermis; however, it appears that a robust supply of papillary fibroblasts may be needed to maintain a youthful-appearing dermal-epidermal junction and the epidermis itself. The present example of skin sites treated with coring needles as described herein has demonstrated a significant amount of cellular activity within this region.

Figure 11:
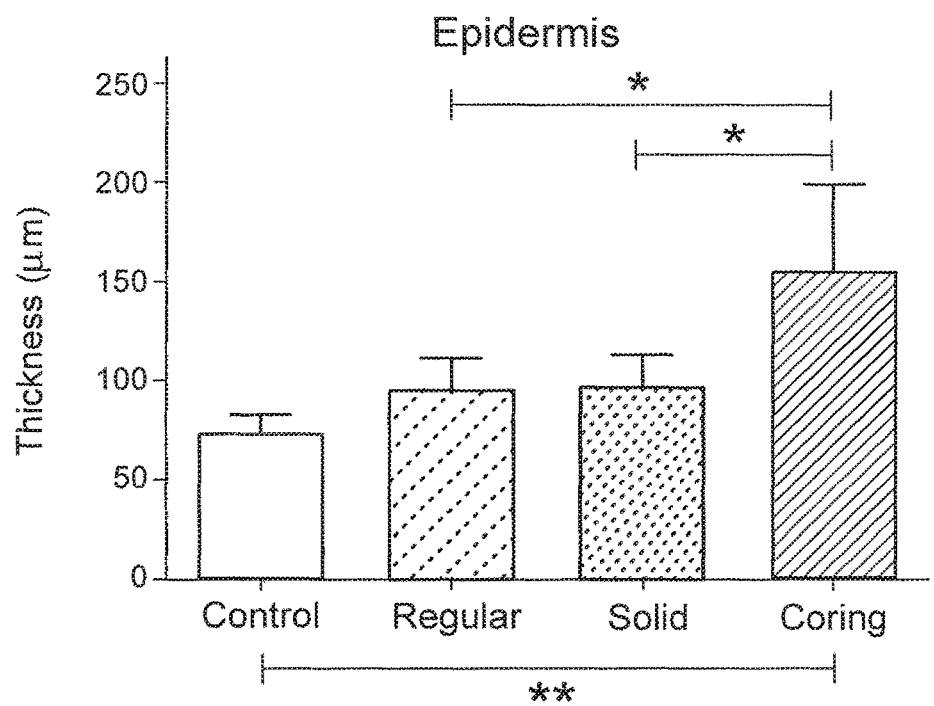
FIG. 11 is a plot of exemplary data showing the observed increase in epidermal thickness of porcine skin damaged with coring needles as compared to other treated and non-treated skin areas.

In addition to a younger-appearing rete ridge pattern and a thicker superficial dermis, the skin sites treated with coring needles exhibited a thicker epidermis at 4 weeks after treatment. A graph of epidermal thickness in biopsy samples for a control (untreated) site and for sites treated with the three types of needles, measured 4 weeks after treatment of the sites as described herein, is shown in FIG. 11. The epidermis of the sites treated with the coring needles appear to be significantly thicker (187%) than the control sites ($p<0.01$) in this figure.

Collagen content for each treatment site was assessed at 12 weeks after the treatment of the various skin sites with the needle devices. 4 mm punch biopsies were digested in a solution of 10 ml of 0.5M acetic acid and Pepsin 0.1 mg/ml (Sigma Aldrich, St. Louis, Mo.) overnight at 4° C. Samples were homogenized using a TissueRuptor (Quiagen, Hilden, Germany). The protocol for the Sircol Soluble Collagen Assay (Biocolor, Carrickfergus, UK) was then followed using a 1/1000 initial dilution. Absorbance was determined using a Spectramax M2 microplate reader (Molecular Devices, Sunnyvale, Calif.).

Figure 12:
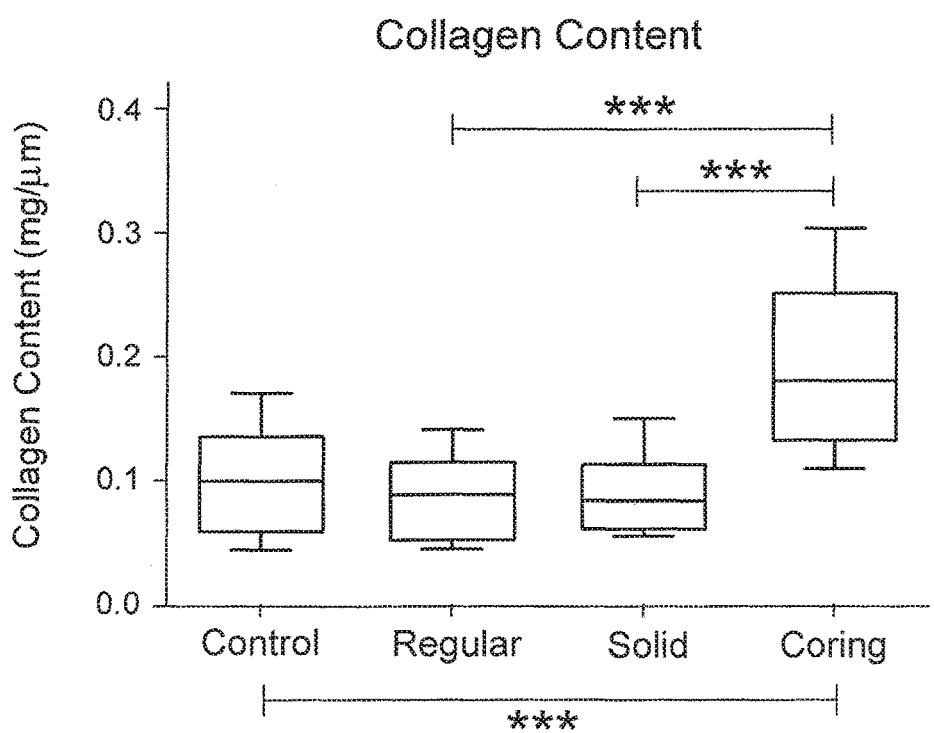
FIG. 12 is a plot of exemplary data showing the observed increase in collagen content of porcine skin damaged with coring needles as compared to other treated and non-treated skin areas.

A plot of the measured collagen content in control (untreated) sites and in sites treated with the three types of needles, 12 weeks after treatment of the skin sites, is shown in FIG. 12. In total, the sites treated with coring needles had a mean collagen content that was 89% higher than that of the control (untreated) sites ($P<0.001$). This average collagen level was also significantly higher than that measured in sites treated with either the regular hypodermic needles or the solid needles, as shown in FIG. 12.

The collagen assay results are consistent with observation of significant collagen neogenesis around the regions of skin that were removed with the coring needles. This collagen production was also observed to a lesser extent in tissue treated with the solid needles. The production of new collagen has been correlated with a clinical improvement of aged or photo-aged skin. The creation of new, fine, compact collagen has been observed in numerous laser studies and may be most important hallmark of skin rejuvenation. An 89% increase in collagen content was detected by ELISA techniques, 12 weeks after treatment, in the sites treated with coring as compared to the control (untreated) sites.

In summary, an exemplary embodiment of method and apparatus has been tested that includes mechanical removal of small columns of skin tissue using one or more coring needles as described herein. Immediately following the removal of multiple small tissue cores from a skin site, erythema and serous oozing were observed that is substantially similar to that observed after generating a similar density of piercings with similarly-sized solid (non-coring) needles. The erythema generated by the coring devices and procedures described herein is also similar to that observed following a high-density laser fractional resurfacing treatment. However, the coring sites were observed to be quickly re-epithelialized and return to normal skin coloration within one week, which can result in part from the minor degree and distributed geometry of epidermal damage.

The exemplary results indicate that significant amounts of tissue can be removed with coring needles, without creating scar or leading to any other adverse advent. For example, embodiments of the present invention can provide cleanly cored tracts that lead to changes in skin architecture and collagen content, with no observable cellular infiltrate or significant inflammation. Despite an observed increase in fibroblast activity and collagen neogenesis at one week and one month after treatment, the cored skin contained only scattered macrophages and lymphocytes. In contrast, fractional ablative lasers tend to produce a vigorous inflammatory response and a neutrophilic infiltrate around the necrotic channels in both humans and pigs with a coagulation zone that reaches about 65 microns in thickness, as well as increased infiltrate, micro thrombosis and sclerosis of vessel walls when using moderate laser flux. having been observed for greater than 6 months after fractional laser treatment. Further, the lack of inflammation or expression of heat shock proteins following procedures according to embodiments of the present invention may lead to a more rapid recovery and decreased adverse effects as compared to conventional laser-based resurfacing procedures.

Although commonly employed as a large animal model for skin rejuvenation, the pig is a poor comparison to humans, as they do not exhibit human like wrinkles, photodamage or similar skin vasculature. The test pig had neither aged nor lax skin, thus there was little chance for us to demonstrate any gross improvement in texture over our untreated sites.

The needle-based rejuvenation procedure described herein was well tolerated, with none of the treatment sites showing any sign of infection or scar. The sites healed quickly, with re-epithelialization within 1 week and resolution of erythema by 2 weeks after treatment. Sites treated with coring needles exhibited significant thickening of the papillary dermis and epidermis, as well as enhanced undulating rete ridges increasing the epidermal-dermal junction—a sign of youthful skin. These sites also exhibited newly aligned and augmented elastic fibers and a significant increase in collagen content as compared to untreated sites.

The coring needle-based skin rejuvenation method and apparatus as described herein was observed to be safe and effective for inducing the microscopic and biologic endpoints of skin rejuvenation, and more effective than similar procedures and devices that use other needle types. Accordingly, embodiments of the present invention can provide a new modality for the safe and cost-effective treatment of age-related rhytides, skin laxity, photo damage, scarring and striae.

The foregoing merely illustrates the principles of the present invention. Other variations to the disclosed embodiments can be understood and effected by those skilled in the art in practising the claimed invention from a study of the drawings, the disclosure, and the appended claims. In the claims, the word "comprising" does not exclude other elements or steps and the indefinite article "a" or "an" does not exclude a plurality. The mere fact that certain measures are recited in mutually different dependent claims does not indicate that a combination of these measures cannot be used advantageously. Any reference signs in the claims should not be construed as limiting the scope of the claims. Various modifications and alterations to the described embodiments will be apparent to those skilled in the art in view of the teachings herein. It will thus be appreciated that those skilled in the art will be able to devise numerous techniques which, although not explicitly described herein, embody the principles of the present invention and are thus within the spirit and scope of the present invention. All references cited herein are incorporated herein by reference in their entireties.

What is claimed is:

1. An apparatus for producing a cosmetic effect in a skin tissue, comprising:
   at least one hollow needle comprising a distal end thereof, wherein the at least one hollow needle is configured to remove portions of the skin tissue when the hollow needle is repeatedly inserted into and withdrawn from the skin tissue, so as to produce the cosmetic effect, and wherein
   the apparatus further comprises:
   a) a filter arrangement and container for capturing the portions of the skin tissue to be discarded; and
   b) a reciprocating arrangement configured to translate the hollow needle over the skin tissue in one direction or two orthogonal directions
   wherein the apparatus is programmed to produce an array pattern in the skin tissue by removing the portions of the skin tissue.

2. The apparatus of claim 1, wherein the at least one hollow needle comprises one, two, or three or more prongs at the distal end of the hollow needle.

3. The apparatus of claim 2, wherein the apparatus comprises a plurality of hollow needles.

4. The apparatus of claim 3, wherein adjacent hollow needles of the apparatus have a distance of:
   (i) about 15 mm or less;
   (ii) about 10 mm or less; or
   (iii) about 5 mm or less.

5. The apparatus of claim 1, wherein the at least one hollow needle:
   (a) has an inner diameter of:
      (i) less than about 0.5 mm; or
      (ii) between about 0.24 mm and 0.4 mm; or
      (iii) between about 0.3 mm and 0.5 mm, or
   (b) has a gauge size between about 22 and 25, or
   (c) has a length between about 2 mm and about 5 mm, or
   (d) is configured to extend through the entire dermis to at least a depth of a subcutaneous fat layer.

6. The apparatus of claim 1, wherein the at least one hollow needle comprises a lumen and at least one protrusion provided within the lumen, optionally, wherein the protrusion is angled upward and is configured to grab onto and pull the portion of the skin tissue from the surrounding skin tissue when the at least one hollow needle is withdrawn from the skin tissue.

7. The apparatus of claim 1, wherein the at least one hollow needle further comprises at least one angled notch provided in a wall of the hollow needle, optionally, wherein an edge of the at least one angled notch protrudes outward beyond an outer periphery of the at least one hollow needle.

8. The apparatus of claim 1, wherein the distal end of the at least one hollow needle comprises a sharpened edge and wherein the sharpened edge is configured to facilitate insertion of the hollow needle into the skin tissue.

9. The apparatus of claim 1, wherein the reciprocating arrangement:
   (i) is configured to displace the at least one hollow needle back and forth along a direction substantially parallel to the axis of the hollow needle; or
   (ii) comprises a motor, an actuator, or both; or
   (iii) is enclosed in a housing.

10. The apparatus of claim 9, wherein the housing is configured to stretch or stabilize the skin tissue proximal to the at least one hollow needle, to reduce deformation of the skin tissue, or to improve accuracy of the insertion of the at least one hollow needle into the skin tissue.

11. The apparatus of claim 1, further comprising one or more of the following:
   (i) a substrate, wherein the at least one hollow needle is coupled to the substrate; or
   (ii) a handle; or
   (iii) a speed sensing arrangement, wherein the speed sensing arrangement is configured to control a reciprocating frequency of the at least one hollow needle; or
   (iv) a position sensing arrangement, wherein the position sensing arrangement is configured to control the insertion position of the at least one hollow needle into the skin tissue; or
   (v) a low-pressure conduit, wherein the low-pressure conduit is connected to a low pressure source to generate a suction in the at least one hollow needle, optionally, wherein the low-pressure source is a vacuum pump or a piston; or
   (vi) a heat source, wherein the heat source is connected to the at least one hollow needle and is configured to remove portions of the skin tissue from the hollow needle, optionally, wherein the heat source is a resistive heater or current; or (vii) a source of pressurized fluid, wherein the pressurized fluid is connected to the at least one hollow needle and is configured to clean or flush out portions of the skin tissue from the hollow needle, optionally, wherein the pressurized fluid is saline.

12. The apparatus of claim 11, wherein the substrate:
(i) is configured to repeatedly insert and withdraw the at least one hollow needle from the skin tissue in a stamping mode; or
(ii) comprises a flat or curved lower surface, wherein the lower surface is configured to match a contour of the skin tissue, and optionally, wherein the at least one hollow needle is configured to extend between about 2 mm and 5 mm below the lower surface of the substrate; or
(iii) is substantially cylindrical and configured to roll over a surface of the skin tissue.

13. The apparatus of claim 11, wherein the low pressure conduit is configured to facilitate insertion of the at least one hollow needle into the skin tissue or removal of portions of the skin tissue from the hollow needle.

14. A method for removing aged or damaged skin tissue, comprising: producing a plurality of holes in the skin tissue by removing portions of the skin tissue using the apparatus of claim 1, and discarding the removed portions of the skin tissue, wherein the method promotes the growth of new skin components or reduces scarring, age-related rhytides, skin laxity, photo damage, or striae.

15. The method of claim 14, wherein an areal fraction of about 0.1 of the skin tissue is removed.

16. The method of claim 14, wherein the at least one hole has a depth:
(i) between about 2 mm and about 5 mm; or
(ii) that extends through the entire dermis to at least a depth of a subcutaneous fat layer.

17. The method of claim 14, wherein the at least one hole has a diameter:
(i) less than about 0.5 mm; or
(ii) between about 0.24 mm and 0.4 mm; or
(iii) between about 0.3 mm and 0.5 mm.

18. The method of claim 14, wherein the adjacent holes formed by the apparatus have a distance of:
(i) about 15 mm or less; or
(ii) about 10 mm or less; or
(iii) about 5 mm or less.

19. The method of claim 14, wherein the plurality of holes in the skin tissue produce an array pattern, optionally, wherein the array pattern comprises one or more rows, a two-dimensional pattern, or a random distribution, optionally, wherein the two-dimensional pattern is a square, rectangle, triangle, or hexagon.

* * * * *